US00PP21593P2

(12) United States Plant Patent
Colfer

(10) Patent No.: US PP21,593 P2
(45) Date of Patent: Dec. 28, 2010

(54) ARTICHOKE PLANT NAMED 'PS-MSC0204'

(50) Latin Name: *Cynara cardunculus*
Varietal Denomination: PS-MSC0204

(75) Inventor: William J. Colfer, Aptos, CA (US)

(73) Assignees: Plant Sciences, Inc., Watsonville, CA (US); Ocean Mist Farms, Castroville, CA (US)

( * ) Notice: Subject to any disclaimer, the term of this patent is extended or adjusted under 35 U.S.C. 154(b) by 0 days.

(21) Appl. No.: 12/584,742

(22) Filed: Sep. 11, 2009

(51) Int. Cl.
*A01H 5/00* (2006.01)

(52) U.S. Cl. ..... Plt./258

(58) Field of Classification Search ..... Plt./258
See application file for complete search history.

*Primary Examiner*—Susan B McCormick Ewoldt
(74) *Attorney, Agent, or Firm*—Foley & Lardner LLP

(57) ABSTRACT

A new and distinct *Cynara cardunculus* L. cultivar of artichoke plant named 'PS-MSC0204', characterized by its fleshiness of bracts; fleshiness of hearts; uniformity of head shapes; and male sterility which is demonstrated by the absence of pollen on all florets during anthesis.

3 Drawing Sheets

Latin name of the genus and species of the plant claimed: *Cynara cardunculus*.

Variety denomination: 'PS-MSC0204'.

BACKGROUND OF THE INVENTION

The present invention comprises a new and distinct cultivar of artichoke plant, botanically known as *Cynara cardunculus* L., and herein referred to by the cultivar name 'PS-MSC0204'.

*Cynara cardunculus* L., commonly known as Globe artichoke, is a thistle-like perennial herb and is a member of the family *Asteraceae*. Globe artichokes comprise: leaves, which are pinnately lobed; but primarily spiney; oval capitula composed of overlapping layers of bracts surrounding a large number of florets; and receptacles, which are enlarged and fleshy. Globe artichoke plants may be propagated by division or vegetative means, and are essentially grown for the production of the immature flower heads, which are considered as vegetable delicacies. Fresh artichokes may be baked, steamed, or boiled, after which the fleshy receptacle, inner and outer bracts, and parts of the floral stem may be eaten.

The new artichoke cultivar is a product of a planned breeding program carried out by the inventor, William J. Colfer, in Chowchilla, Calif., in 2004. The new artichoke cultivar 'PS-MSC0204' is a result of a controlled cross between the female (seed) parent, *Cynara cardunculus* L. designated 'CTMS2C' (unpatented) and the male (pollen) parent, *Cynara cardunculus* L. designated 'CT' (unpatented) The new artichoke 'PS-MSC0204' was discovered and selected by the inventor, as a single flowering plant within the progeny of the stated cross in a controlled environment in 2004 in Chowchilla, Calif.

Asexual reproduction of the artichoke 'PS-MSC0204' by vegetative cuttings was first performed in August of 2004 in Castroville, Calif., and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'PS-MSC0204', which in combination distinguish this artichoke as a new and distinct cultivar:

1. Fleshiness of bracts;
2. Fleshiness of hearts;
3. Uniformity of head shapes; and
4. Male sterility which is demonstrated by the absence of pollen on all florets during anthesis.

It should be noted that these data were collected from first year transplants.

Plants of the new *Cynara* 'PS-MSC0204' differ from plants of the parents, 'CTMS2C' (unpatented) and 'CT' (unpatented) in the following characteristics described in Table 1.

TABLE 1

| Characteristic | New Cultivar 'PS-MSC0204' | Female Parent 'CTMS2C' (unpatented) | Male Parent 'CT' (unpatented) |
|---|---|---|---|
| Average Head Number | 6.80 | 4.8 | 6.4 |
| Head Shape | Oval | Oval | Slightly rounded to oval |
| Head Exterior Color | 5 GY 5/4-5 GY 5/6 | 5 GY 5/4-5 GY 4/4 | 5 GY 4/4-5 GY 5/6 |

Of the many commercial cultivars known to the present inventor, the most similar in comparison to the new *Cynara* 'PS-MSC0204' is Cynara 'GREEN GLOBE' (unpatented), in the following characteristics described in Table 2:

TABLE 2

| Characteristic | New Cultivar 'PS-MSC0204' | Comparison Cultivar Name GREEN GLOBE (unpatented) |
|---|---|---|
| Average Head Number | 6.8 | 5.2 |
| Head Exterior Color | Green (slightly glossy) | Green (no glossiness) |
| Average Fleshiness of Bract | About 0.43 cm | About 0.49 cm |

For identification, a series of AFLP molecular markers have been determined for this new artichoke cultivar.

BRIEF DESCRIPTION OF THE PHOTOGRAPHS

The accompanying photographs illustrate the overall appearance of the new artichoke 'PS-MSC0204' showing the colors as true as is reasonably possible with colored reproductions of this type. Colors in the photographs may differ slightly from the color values cited in the detailed botanical description, which accurately describe the color of 'PS-MSC0204'. The depicted plant and plant parts of the new artichoke 'PS-MSC0204' were taken in Madera County, Calif. of first year transplants.

DETAILED BOTANICAL DESCRIPTION

Figure 1:
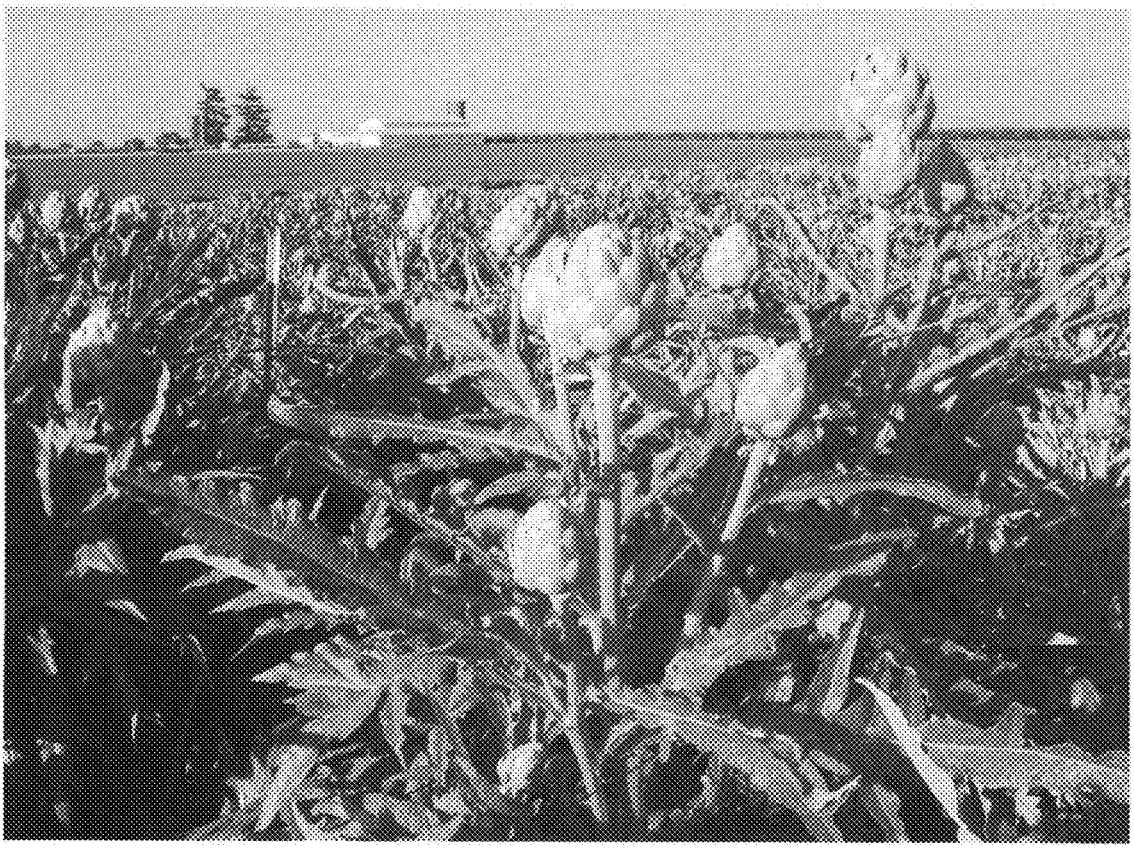
FIG. 1 shows a close-up, side view perspective of 'PS-MSC0204' plants grown in the field.
Figure 2:
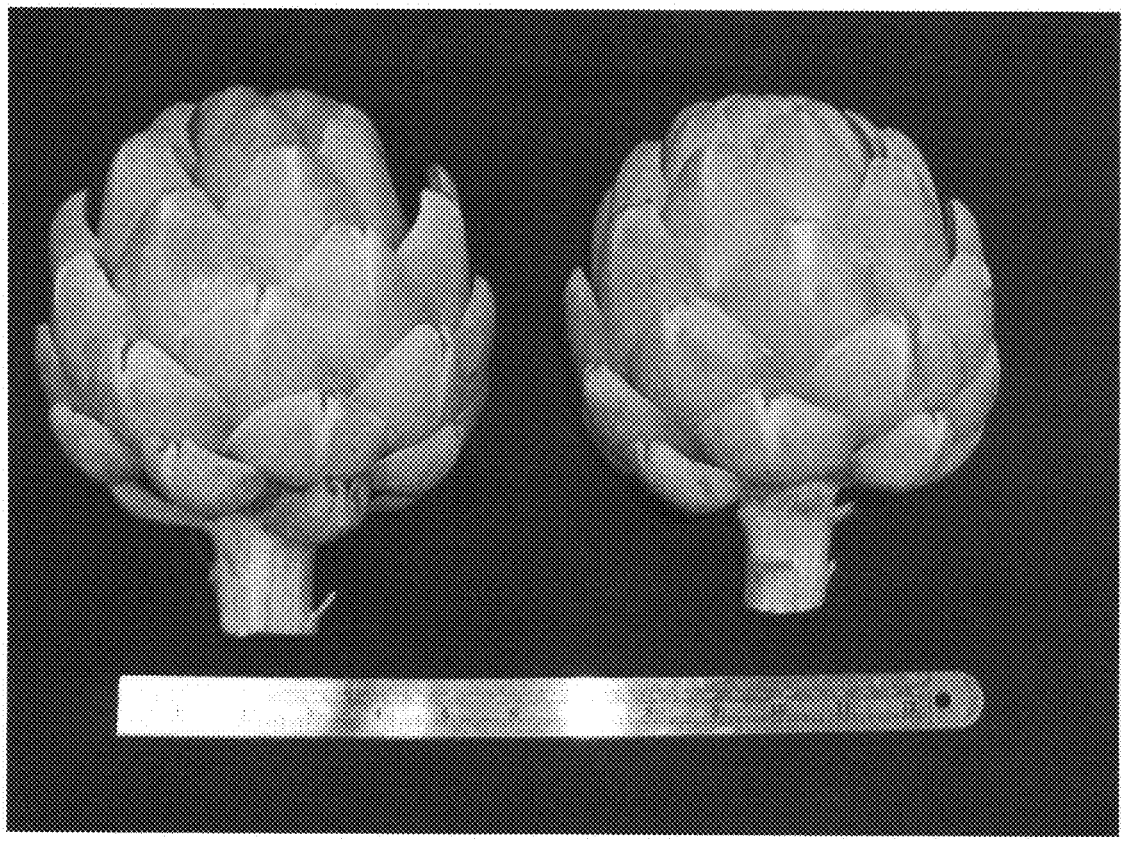
FIG. 2 shows a close-up perspective of the side view of the exterior of a typical mature fruit of 'PS-MSC0204'.
Figure 3:
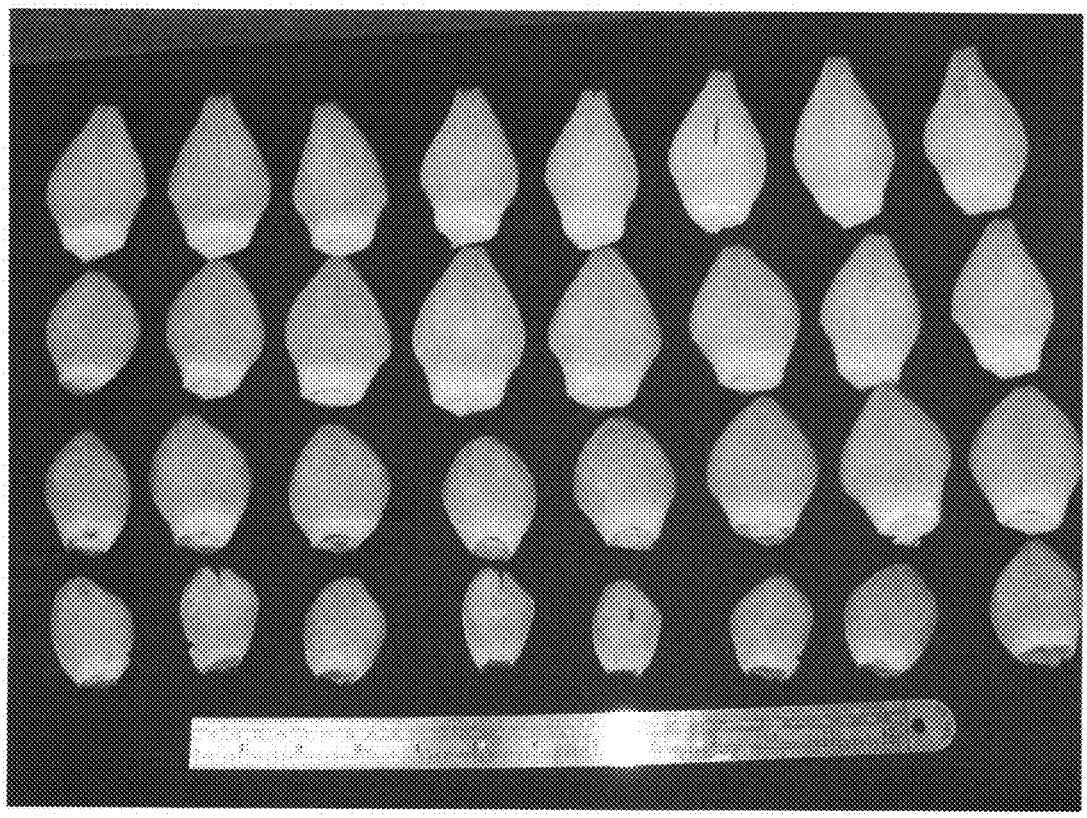
FIG. 3 shows a close-up perspective view of the interior surface of the outer bracts of a typical mature fruit of 'PS-MSC0204'.

The new artichoke 'PS-MSC0204' has not been observed under all possible environmental conditions. The phenotype of the new cultivar may vary with variations in environment factors, including weather (temperature, humidity, and light intensity), day length, soil type, and location, without any change in the genotype of the plant.

The aforementioned photographs, together with the following observations, measurements and values describe plants of 'PS-MSC0204' as grown in Castroville, Calif., under conditions which closely approximate those generally used in horticultural practice.

Castroville is located in California's central coast. Conditions can vary greatly during the summer months. Air temperature can range between the low 20's (degrees Fahrenheit) in the winter to above 80 (degrees Fahrenheit) during the summer months. Relative humidity is generally moderate with values ranging from the mid 40's to the high 60's. Prevailing winds are westerly, and rainfall rarely exceeds 25" (inches) of rainfall.

In the following description, holding quality was measured by the physical appearance of the harvested heads. This includes the heads appearance following 3, 7 and 10 day storage periods in a cold storage room held at 34 (degrees Fahrenheit). Head exterior (oxidation) was observed at each of the three observation points. Browning and blackening of plant tissue was evaluated as light, moderate and extreme. Juiciness was measured by observing exudate and rated as absent, moderate or excessive. Overall storage response was measured by observations concentrated on visible color variability and/or presence of lesions or other cosmetic anomalies. Leaf ratio (L/W) was determined by dividing representative leaf sample length measurements by representative leaf sample width measurements. Finally, head response to (weather) was determined by observing the heads at maturity. These field observations focus on presence or absence of bronzing, necrotic and chlorotic lesions or any abiotic response to environmental conditions. These data are reported as the possible causal event(s), and then describe the detailed head and plant responses.

The age of the plants in the aforementioned photographs, together with the following observations, measurements and values describe plants of 'PS-MSC0204' about 1095 to 1460 days from transplanting. Plants were developed in transplant trays for about 120 to 150 days, for a total plant age of about 270 to 330 days. Not all greenhouse plantings are performed on the same day. Physical data collection may also be performed on different days.

All color references below are measured against The Munsell Book of Color, Munsell Color Macbeth Division of Kollmorgen Instruments Corporation, (1988/PRO88-A). Colors are approximate as color depends on horticultural practices such as light level and fertilization rate, among others.

Classification:

*Botanical.*—*Cynara cardunculus* L.

Parentage:

*Female or seed parent.*—*Cynara cardunculus* L. designated 'CTMS2C' (unpatented).

*Male or pollen parent.*—*Cynara cardunculus* L. designated 'CT' (unpatented).

Propagation: Vegetative cuttings (side-shoots selected and harvested from original parent selection).

Plant:

*Height.*—About 158.13 cm. Range: 140.10 cm to 180.00 cm.

*Width.*—About 186.5 cm. Range: 173.2 cm to 200.00 cm.

*Growth habit.*—Upright/intermediate.

*Vigor.*—Good. (This measurement is based on overall plant performance. Including plant height, density of leaf canopy and overall plant growth and development rates).

Lateral shoots: These offshoots or suckers from axillary buds are borne at the base of the stem just below the soil surface.

*Number per plant.*—About 1.0 or 6.0 per plant.

*Length.*—About 12.94 cm. Range: 10.2 cm to 16.4 cm.

*Diameter.*—About 3.75 cm. Range: 1.7 cm to 2.4 cm.

*Color.*—2.5 GY 5/6-2.5 GY 6/6. Anthocyanin coloration range: 5R 3/4-7.5R 5/4.

*Foliage density.*—Open to moderate, variable shoots give plant an open to moderate plant density appearance.

*Side shoot development.*—Moderate side shoot development. Plant responds to floral stalk removal inducing side-shoot development.

*Number of leaves per side shoot.*—Ranges from 3 to 6.

Stem (main):

*Length.*—About 12.88 cm. Range: 8.3 cm to 26.2 cm.

*Diameter.*—About 6.22 cm. Range: 5.3 cm to 7.2 cm.

*Width* (*with leaves*).—Ranges from 6.3 cm to 8.2 cm.

*Color.*—Color designation: 5 GY 6/6-5 GY 7/6. Basal anthocyanin coloration: 5R 3/4-7.5R 6/4.

*Texture.*—Stem texture can vary from areas that are tomentum to tomentose. Maturity and presence of surrounding leaf tissue influence stem pubescence.

*Number of leaves per main stem.*—Ranges from 12 to 16.

*Distance between leaf lobes (use petiole or leaf insertion not lobes)on stem.*—Ranges from 8.2 cm to 14.4 cm.

*Internode length.*—Ranges from 6.8 cm to 12.4 cm (Internode length influenced by soil conditions (moisture) in the field.

Buds:

*Shape.*—Typically ovate. Range from slightly round to oval.

*Height.*—Ranges 15.24 cm to 18.54 cm.

*Diameter.*—Ranges 17.27 cm to 18.03 cm.

*Color.*—Color dependent on age and exposure to sun Range: 5 GY 5/4-5 GY 5/6.

*Texture.*—Glabrous, with some light pubescence at the base of the buds.

Inflorescence: Mature, meaning grown to point of harvest and ready for consumption.

Florets:

*Number per primary head.*—Range of about 1020 to 1326.

*Overall shape.*—Tubulose, fused basal region; anther tubes that flare slightly to a flattened, expanded obtuse apex stigmatic region.

*Width.*—About 1.5 mm.

*Color.*—Purple, color dependent on floret age. Range: 5P 3/10-5P 3/8-5P 3/6. Florets oxidize to darker stigmatic colors and lighter anther colors late in maturation.

*Margin.*—Entire.

*Texture.*—Smooth.

Capitulum (head):

*Number.*—About 6.80/plant. Range: 5.0 to 8.0 heads/plant.

*Shape.*—Predominately oval shapes, and slightly broadened mid-sections, creating rounded to oval shape.

*Size.*—(12) Primary: 36.20 cm to 38.10 cm. (18) Secondary: 28.58 cm to 30.40 cm. (30) Tertiary: 28.58 cm to 30.48 cm. (36) Tertiarty: 26.04 cm to 27.94 cm. (48) Tertiarty: 23.50 cm to 25.40 cm.

*Texture.*—Intermediate, smooth and glossy.

*Color.*—Range: 5 GY 5/4-5 GY 5/6.

*Fragrance.*—Mild, lightly aromatic. Slightly sweet aroma, freshly cut — green grass aroma.

*Firmness.*—Heads are firm. Some head types in the spring have reduced firmness.

*Gloss.*—Glossy green/yellow coloration. Heads have distinct overall sheen.

*Juiciness.*—Some interior bracts have exudate visible. Most outer bracts and peduncle tissues are absent of exudate.

Peduncle:

*Length.*—Ranges 10.41 cm to 18.42 cm.

*Diameter.*—Ranges 2.79 cm to 3.43 cm.

*Color.*—Range: 5 GY 6/6-5 GY 6/6-5 GY 7/8. Pubescence density influence the color range.

*Texture.*—Early development can be tomentose while later development can be delicately tomentose. Distinct bands or grooves are also evident; running the length of the peduncle.

Bract:

*Number.*—About 70.50 bracts. Range: 65 to 86 bracts.

*Arrangement.*—Bracts layer and overlap attaching to a fleshy receptacle.

*Length.*—Outer: About 6.86 cm; Range: 4.57 cm to 8.13 cm. Inner: About 8.89 cm; Range: 8.64 cm to 9.40 cm.

*Width.*—Outer: About 5.72 cm; Range: 4.57 cm to 5.84 cm. Inner: About 4.91 cm; Range: 3.20 cm to 4.60 cm.

*Shape.*—Bracts are predominantly oval shaped with slightly constricted (narrow) basal regions on inner bracts and outer bracts are slightly rounded at the base.

*Texture.*—Smooth, slight texture.

*Color (inner) (position in capitulum).*—Bract interior coloration: 2.5 GY 9/2-2.5 GY 9/4 (Green coloration). Outer bract interior coloration (apex): 5 GY 7/4-5 GY 7/6 (Green - Yellow Coloration). No anthocyanin coloration present in innermost interior bract margins.

*Color (outer)) (position in capitulum).*—5 GY 5/4-5 GY 5/6 (Green Coloration). Mid-region to base: 2.5 GY 5/8-2.5 GY 5/6-2.5 GY 6/6 (Green coloration with basal yellow coloration).

*Firmness.*—Moderate. Bracts are brittle with reduced malleability. Outer bracts are more flexible.

*Spinosity.*—Present on bract apexes. Spines are slightly notched and splitting. Length ranges between 1.5 mm to 3.0 mm in length.

*Basal thickness.*—About 4.28 mm. Range: 3.33 mm to 4.67 mm.

Heart:

*Description.*—Concave, full. Heart is slightly concave with moderate outer margins.

*Color.*—5 Y 9/1-5 Y 9/2.

Pappus:

*Number.*—The pappus attaches at the apical region of the mature seed. Approximately 76-84 pappus filaments per seed. Seed numbers vary — about 1020 to 1326 seeds per head. The seed numbers vary greatly; dependent upon weather conditions, pollination, fertilization and seed-set which consequently influence pappus numbers.

*Length.*—About 28.0 mm. Range: 16.0 mm to 29.0 mm.

*Color.*—Variable white coloration. ~2.5Y 8/4 (base)-5.5Y 9/2 (apex) (colors difficult to match).

Overall cold storage response: Good cold storage response. Slight oxidation observed (light browning).

Cold storage (hold quality): Moderate. Some outer bract brown lesions are visible with slightly necrotic bract tips.

Head exterior (oxidation): Only those areas damaged during harvest showed some oxidation. Some bract margins are slightly discolored.

Head response (weather): None. Some exterior head damage was observed. Some adverse head damage was observed from abrasion with other surrounding heads.

Foliage:

Leaf:

*Shape.*—Irregular, dentate leaves that are long and straplike, parted pinnatisect margins, and a slightly reduced tomentose upper leaf surface and more advanced tomentose lower leaf surface. The leaf apex is described as a reduced mucronulate.

*Length.*—About 92.78 cm. Range: 89.3 cm to 95.6 cm.

*Width.*—About 53.18 cm. Range: 52.60 cm to 53.60 cm.

*Leaf ratio (L/W).*—About 1.74. Range: 1.67 to 1.79.

*Leaf area.*—About 4,939.06 $cm^2$. Range: 4764.00 $cm^2$ to 5117.00 $cm^2$.

*Leaf serrations.*—About 36.03 mm. Range: 31.3 mm to 40.3 mm.

*Leaf distance between serrations.*—About 47.67 mm. Range: 38.33 mm to 51.67 mm.

*Leaf basal angle.*—About 41.30°. Range: 55.0° to 41.3°.

*Leaf basal thickness.*—About 5.17 mm. Range: 5.00 mm to 7.00 mm.

*Texture.*—Mature leaves are more blistered and rough textured. Younger, developing leaves are smooth and lack the blistered texture.

*Pubescence.*—Smooth to sparse density. Pubescence on most leaves is indistinct. Immature, younger leaves are moderately pubescent.

*Color* (*mature*).—Upper surface. Range: 5 GY 4/4-5 GY 4/6-5 GY 4/8. Lower surface: Range: 5 GY 4/4-5 GY 5/4.

*Color* (*immature*).—Upper surface. Range: 5 GY 4/6-5 GY 3/6. Lower surface: Range: 5 GY 5/4-5 GY 4/4.

Lobes:

*Number per leaf.*—About 4 to 8. (This number can also vary and is influenced by soil types and winter growth conditions) Apex Shape: Apex can vary obtuse to acute depending on leaf maturity and developmental stages in relation to reproductive bolting.

*Base shape.*—Generally described as pinnatisect and lobed.

*Length.*—Ranges 31.3 cm to 40.3 cm. (Dependent upon leaf developmental stages)

*Width.*—Ranges 3.30 cm to 5.30 cm.

Venation: Basal regions of the leaf have slightly green coloration. The terminal and apical regions coloration is white. Both mid-vein and surrounding venation is white colored.

*Pattern.*—White mid-vein with white color venation radiating from leaf mid-vein. Venation pattern is described as pinnate.

*Color.*—White, closest to 5 GY-9/1; 10Y 9/1; 5Y 9/1.

Petiole:

*Length.*—About 4.22 cm. Range: 3.90 cm to 6.42 cm.

*Width.*—About 2.54 cm. Range: 2.47 cm to 2.67 cm.

*Diameter.*—About 3.03 cm. Range: About 2.8 cm to 3.4 cm.

*Color.*—5 GY 6/4-5 GY 6/6.

Reproductive organs/seeds: Seed are generally a dark tan color with variable black specks on the seed coat. Seed has an elongated oval (obtuse/rounded basal apex) shape. About 4-5 mm (w)×8-9 mm (1)).

Weather tolerance: No testing has been.

Disease/pest resistance: No observations made.

Disease/pest susceptibility: No observations made.

General observations: This new artichoke hybrid is a unique type that exhibits the following characteristics. The plants moderate height, ranging from 140 cm to 180 cm. Its comparative head qualities to California's artichoke variety 'GREEN GLOBE' (unpatented): green (slightly glossy) (unlike Green Globe) exterior coloration, smaller head numbers. Head numbers ranging from 5-8 heads per plant. Head shape does have slight variation displaying a predominately oval shapes and, slightly broadened mid-sections, rounded - oval shapes. These slightly glossy heads are produced in the sizes ranging from (12) primary, size (18) secondaries and size (30, 36 and 48) tertiaries. Floral stalk development and head numbers can vary. Anthocyanin coloration is not present in innermost interior bract margins. The head spinosity is present on bract apexes. Inner bracts also display spines but can be very slightly notched and splitting. The average spine length ranges between 1.5-3.0 mm. The plants upright growth habit is intermediate, but is very vigorous. The canopies coloration is a deeper green/yellow color. These colors on Munsell Leaf Color Chart range from 5 GY 4/4-5 GY 4/6-5 GY 4/8. Leaf spinosity is light to moderate, categorized as few. Floral stalk development during anthesis produces a purple flower. Flower color varies with flower maturity. The phenotypic characteristics of this cultivar may vary slightly, depending upon variation in the environmental factors. Including weather (temperature, humidity and light intensity), day length, soil type, farming practices, location and time of year.

What is claimed is:

1. A new and distinct *Cynara cardunculus* L. cultivar of artichoke plant named 'PS-MSC0204', as herein described and illustrated by the characteristics set forth above.

* * * * *